United States Patent [19]

Usry et al.

[11] Patent Number: 4,538,604
[45] Date of Patent: Sep. 3, 1985

[54] SYSTEM FOR ASSISTING RESPIRATION

[75] Inventors: Joe D. Usry, Midvale; James B. Bunnell, Salt Lake City; Chris G. Faddis, West Valley, all of Utah

[73] Assignee: Bunnel Life Systems, Inc., Salt Lake City, Utah

[21] Appl. No.: 505,816

[22] Filed: Jun. 20, 1983

[51] Int. Cl.$^3$ ............................................. A61M 16/00
[52] U.S. Cl. ......................... 128/204.23; 128/204.25; 128/205.24; 128/911
[58] Field of Search ....................... 128/204.21, 204.23, 128/204.24, 205.25, 207.15, 207.14, 204.25, 207.16, 911; 251/7, 141

[56] References Cited

U.S. PATENT DOCUMENTS

| | | | |
|---|---|---|---|
| 3,653,379 | 4/1972 | Glenn | 128/204.21 |
| 3,831,596 | 8/1974 | Cavallo | 128/204.23 |
| 4,155,356 | 5/1979 | Venegas | 128/207.14 |
| 4,176,671 | 12/1979 | Citrin | 251/7 |
| 4,265,237 | 5/1981 | Schwanbom et al. | 128/205.24 |

FOREIGN PATENT DOCUMENTS 2063686 6/1981 United Kingdom ........... 128/204.25

Primary Examiner—Henry J. Recla
Attorney, Agent, or Firm—Thorpe, North & Western

[57] ABSTRACT

A system for applying to a person's respiratory system pressure pulses having a high energy density. The system includes a manifold for applying gas pulses to the mouth or throat of a person, a first conduit for supplying gas from a gas source to the manifold, and a first valve disposed on the conduit adjacent to the manifold for interrupting the flow of gas through the conduit to thereby produce gas pressure pulses which flow to the manifold and then to the person. A second conduit coupled between the gas source and the manifold is also provided. A second valve is disposed in the second conduit to normally block the flow of gas therethrough and for periodically opening to allow gas to flow to the manifold. A pressure transducer is disposed between the second valve and the manifold for detecting the pressure in the manifold and for supplying a signal to the gas source indicating what the pressure in the manifold is. The manifold includes a first lumen for carrying gas from the gas source to the person, and a second lumen coupled to the second conduit through which the pressure in the manifold is determined.

5 Claims, 2 Drawing Figures

SYSTEM FOR ASSISTING RESPIRATION

BACKGROUND OF THE INVENTION

This invention relates to a new and improved method and apparatus for applying air pressure pulses to a person's respiratory system to assist ventilation and respiration.

It has been found that persons with various respiratory problems and illnesses can be benefitted by application to the person's respiratory system of rapid, positive pressure pulses of oxygen and air. This type of "ventilation" is superior to the more conventional method of ventilation which consisted of application of relatively large volumes of oxygen and air to a person at frequencies which coincided substantially with the inhalation frequency of the person. Some of the problems with this conventional technique are that those areas of the lung with the least blood perfusion may be preferentially ventilated, added resistance to blood flow into the thorax and pulmonary capillaries is imposed, and blood pressure is oftentimes altered. In addition, the decreased compliance of the lungs of those persons who suffer from respiratory distress syndrome causes high intrapulmonary pressures to be necessary during the application of the oxygen-air pulses. These high pressures oftentimes produce the side affects of pneumothorax, cerebral hemorrhage and broncho-pulmonary dysplasia, all of which are life threatening and debilitating.

Two prior art methods of applying positive pressure pulses of gas to a patient at a higher than normal rate of inhalation and exhalation are disclosed in U.S. Pat. No. 4,155,356 and U.S. Pat. No. 2,918,917. In the first mentioned U.S. Pat. No. 4,155,356, the object of the method described is to alleviate respiratory problems caused from a collapsed lung passageway which, for example, may result from emphysema. The apparatus and method of U.S. Pat. No. 4,155,356 provide for supplying a series of pressure pulses to the air passageway in question, with the pulses having a certain defined wave form and frequency rate. Further, the person on which the method is used is generally able to inhale but not exhale and so the method is used to assist exhalation only. Thus, U.S. Pat. No. 4,155,356 is not directed strictly to assisting respiration—both inhalation and exhalation—to alleviate respiratory problems.

U.S. Pat. No. 2,918,917 discloses apparatus for "vibrating portions of a patient's airway" at a rate which is greater than the patient's normal rate of inhalation and exhalation. The purpose of this is to exercise and massage the airway and associated organs to thus loosen and remove mucous therefrom. It was also stated in the patent that it was believed that vibrating portions of a patient's airway aided in the breathing function by circulating the gas more thoroughly to and from the walls of the lungs.

In co-pending application, Ser. No. 322,742, now U.S. Pat. No. 4,481,944, a system is described for applying a series of high pressure air pulses to a person's respiratory system, with the frequency of the pulses being varied over some range encompassing the natural or resonant frequency of the person's respiratory system. This system achieves a degree of ventilation of a person's respiratory system not heretofore achieved.

The present invention improves upon and simplifies the above-described system by providing mechanisms which may be readily serviced and replaced, and which delivers high energy density positive pressure pulses to a patient to better ventilate the patient's respiratory system.

SUMMARY OF THE INVENTION

It is an object of the invention to provide a new, simple and easy to manufacture and service apparatus and method for applying high frequency air pressure pulses to a person's respiratory system.

It is also an object of the invention to provide such a method and apparatus which is, in part, self servicing.

It is a further object of the invention to provide new and improved ventilation apparatus having components which may be readily removed and replaced.

It is another object of the invention to provide a method and apparatus for producing positive pressure pulses having high energy density.

It is still another object of the invention to provide such apparatus and method wherein measurement of air pressure pulses delivered to the person can be more accurately made.

The above and other objects of the invention are realized in a specific illustrative embodiment which includes a source of gas under pressure, and an elongate tubular manifold, one end of which is for placement in the mouth and throat of a person to be treated. A valve and conduit couple the other end of the tubular manifold to the source of gas to periodically interrupt the flow of gas to the person. The valve is placed as close to the tubular manifold as possible so that the gas pressure pulses produced by the action of interrupting the flow of gas will be as sharp and as high in energy density as possible. Such gas pressure pulses will provide better ventilation for the person being treated.

In accordance with one aspect of the invention, two lumens are defined in the tubular manifold, a first of which delivers the gas to the person, and a second of which is coupled at one end to a pressure transducer, with the other end terminating near said one end of the manifold. The pressure transducer detects the pressure in the manifold via the second lumen and provides a signal indicating what this pressure is. This signal may be utilized to adjust the pressure of the gas supplied to the manifold to some desired level. The pressure transducer, just as the gas pulse producing valve, is placed as close as possible to the manifold to improve the frequency response of the measurement.

In accordance with another aspect of the invention, a conduit is provided to deliver gas from the gas source to the second lumen to clear out the lumen. A second valve is positioned in the conduit for normally blocking the flow of gas and for periodically opening to allow gas to flow to the second lumen.

BRIEF DESCRIPTION OF THE DRAWINGS

The above and other objects, features and advantages of the invention will become apparent from a consideration of the following detailed description presented in connection with the accompanying drawing in which.

DETAILED DESCRIPTION

Figure 1:
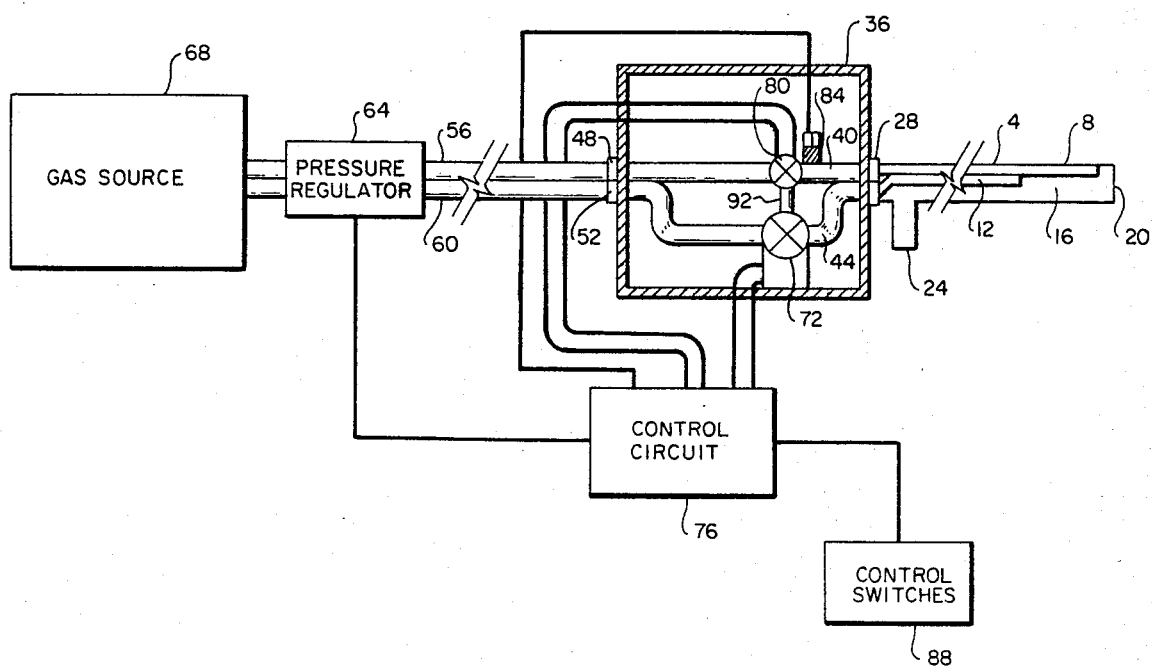
FIG. 1 shows a schematic of apparatus for delivering and thereafter measuring high energy density pressure pulses to a person's respiratory system constructed in accordance with the principles of the present invention.

FIG. 1 shows a schematic of a system for applying a series of high energy density gas pulses to a patient's respiratory system. The system is coupled to the patient by a tubular manifold 4 which is inserted into the mouth and throat of a patient in a conventional manner. The tubular manifold 4 is shown in fragmented form in FIG. 1 and would be long enough and narrow enough for easy insertion into the mouth and throat of a patient.

Defined in the tubular manifold 4 are two lumens or tubes 8 and 12. A third passageway 16 is defined in the tubular manifold 4 to enable communication between the end of the manifold 20 (which is inserted into the mouth of the patient) and an exit opening 24. It is through the passageway 16 that a patient exhales air when undergoing treatment with the apparatus of FIG. 1.

The tubular manifold 4 is coupled by way of a coupling collar or fitting 28 to a housing 36. In particular, the rear end of the manifold 4 is tapered for insertion into the coupling collar 28 and held in place by friction or by a suitable adhesive. The coupling collar 28 is attached to and communicates with a pair of conduits 40 and 44 respectively which are contained in the housing 36. The conduits 40 and 44 extend across the housing and are attached to coupling collars 48 and 52 disposed in the wall on the other side of the housing. Another pair of conduits 56 and 60 are joined to the housing 36 by way of the coupling collars 48 and 52 respectively. Advantageously, the conduits 56 and 60 are tapered for insertion into the collars 48 and 60 where they are held in place by friction. The other end of the conduits 56 and 60 are connected to a pressure regulator 64 which is joined to a source 68 of air and oxygen under pressure.

The air and oxygen source 68 supplies air and oxygen to the pressure regulator 64 which controls the pressure at which the air and oxygen is supplied to conduits 56 and 60. The air and oxygen flows from these conduits through conduits 40 and 44 to lumens 8 and 12 in the tubular manifold 4.

Disposed on the conduit 44 is a valve 72 for periodically interrupting the flow of air and oxygen through the conduit. Operation of the valve 72 is carried out under control of a control circuit 76 which might, for example, be a conventional microprocessor. The control circuit 76 supplies electrical signals to the valve 72 to periodically cause the valve to open and allow the flow of air and oxygen through the conduit 44.

A second valve 80 is disposed in conduit 40 to normally prevent the flow of air and oxygen through the conduit. The valve 80 is also operated under control of the control circuit 76. A pressure transducer 84 is also disposed in the conduit 40 between the valve 80 and the lumen 8. The pressure transducer 84 senses the pressure of the air and oxygen "down stream" of the valve 80 and, in particular, the pressure of the air and oxygen in the tubular manifold 4. The pressure transducer 84 supplies a signal to the control circuit 76 indicating the pressure of the air and oxygen in the manifold. An exemplary pressure transducer is Validyne Engineering Sales Corp., Model DP45.

The control circuit 76, in response to signals from the pressure transducer 84, controls the pressure regulator 64 to maintain a certain desired output pressure. A certain pressure level is generally necessary to properly ventilate a patient, but it is desired that this pressure be minimized to the extent possible while still providing adequate ventilation for the patient. The pressure regulator 64 would typically reduce the pressure of the air and oxygen received from the source 68 from about 50 pounds per square inch to as low as about 2 pounds per square inch. The predetermined pressure level desired for the regulator 64 would be preprogramed into the control circuit 76 via control switches 88.

To obtain an accurate pressure measurement by the pressure transducer 84, the lumen 8 in the tubular manifold 4 is positioned to terminate very near the end of the manifold 20. With this configuration, the pressure of air and oxygen delivered to the patient is more accurately measured. To maintain this accuracy in pressure measurement, it is also important to maintain the lumen 8 and conduit 40 clear of foreign material. For this purpose, valve 80 and conduit 56 are provided so that air and oxygen from the source 68 can be periodically supplied to the conduit 40 and lumen 8 to clear the conduit and lumen. The valve 80 is periodically opened to allow the flow of air and oxygen through the conduit 40 and lumen 8 to clear any foreign material which may have gathered.

Valve 72, which operates which much greater frequency than does valve 80 to produce high frequency pressure pulses for delivery to the patient, may tend to get hot thus increasing the possibility of failure. In order to minimize this problem, a short piece of conduit or tubing 92 is coupled to the conduit 40 and is directed towards the valve 72. Then, when the conduit 80 is periodically opened, air and oxygen are directed both to the lumen 8 and toward the valve 72 to cool the valve. Alternatively, valve 80 could be a three way valve which receives air and oxygen from conduit 56 and directs air and oxygen into conduit 40 and conduit 92.

Figure 2:
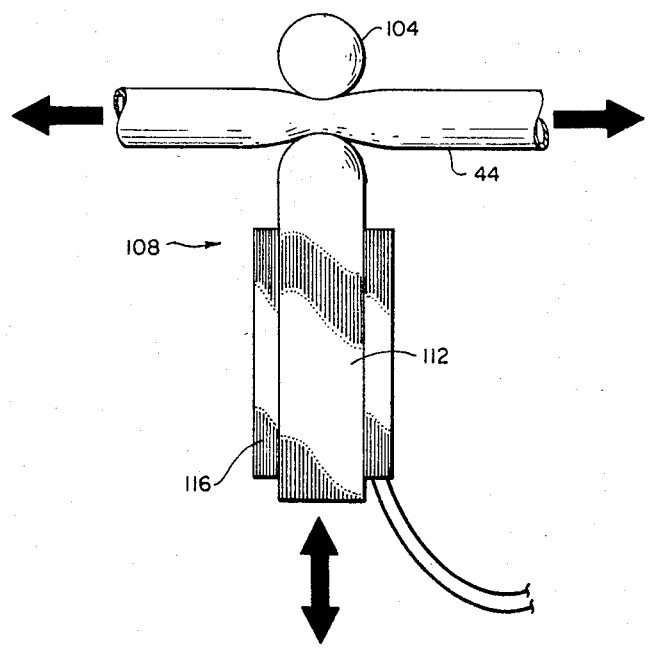
FIG. 2 shows an illustrative valve used in the apparatus of FIG. 1.

FIG. 2 shows an exemplary valve for use as valve 72 in FIG. 1. The valve shown in FIG. 2, since it is not positioned within the conduit through which the air and oxygen flows, is noncontaminating. The valve in question includes a rigid anvil 104 against which a flexible and resilient conduit 44 is positioned. Fixed on the other side of the conduit is a solenoid 108 having a movable armature 112 which, when the winding or coil 116 of the solenoid is energized, is caused to move upwardly towards the anvil 104 to pinch and close the conduit 44. In this manner, the conduit 44 is periodically closed to interrupt the flow of air and oxygen therethrough as described earlier. Since the valve is located externally of the conduit 44, there is no chance that the valve will contaminate the air and oxygen flowing through the conduit. The solenoid 108 may be of conventional design.

High energy density pressure pulses are produced by the apparatus of FIG. 1 by placing the valve 72 adjacent to the tubular manifold. In particular, it has been found that placement of the valve 72 within about six inches of the manifold 4, for a manifold of about six to twelve inches in length, provides the desired pressure pulses. With such placement, the pressure pulses produced by the valve are sharper and have a higher energy density upon reaching the patient than would be the case if the valve were far removed from the patient. The farther away such valve is from the patient, the more the pressure pulse wave front is blunted or dissipated. By providing sharper pressure pulses, greater ventilation is achieved and the overall mean pressure of the pulses supplied to the patient can be reduced. This results in less trauma to the patient.

In a like manner, placement of the pressure transducer 84 adjacent to the tubular manifold 4 provides a more accurate reading and pressure in the manifold since high energy transients are less blunted. Such accuracy in measurement improves control of peak pressure in the development of the pressure pulses and thus safety in operation.

The housing 36, as described earlier, is provide with fittings 28, 48 and 52 which allow for the ready connection and disconnection of the housing with the manifold 4 and with the conduits 56 and 60. With this arrangement, if a failure occurs with either of the valves or with the pressure transducer, the housing 36 can simply be disconnected from the system and a new housing with component parts inserted in its place to allow for repair of the defective parts without interruption of use of the system.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. In an arrangement for assisting a person's respiration including a source of gas under pressure, apparatus for delivering gas pressure pulses to a person's respiratory system comprising an elongate, tubular manifold, a first end of which is for insertion into the mouth and throat of the person and a second end adapted to extend from the mouth of the person, a first lumen defined in the manifold, one end of which terminates a distance from the first end of the manifold and the opposite end of which terminates adjacent the second end of the manifold, a second lumen defined in the manifold, one end of which terminates nearer the first end of the manifold than does the first lumen and the opposite end of which terminates adjacent the second end of the manifold, first conduit means coupled to a second end of the manifold for supplying gas from the source to said opposite end of the first lumen, first valve means disposed in said conduit means adjacent to said second end of said manifold for interrupting the flow of gas through the conduit means to thereby produce gas pressure pulses which flow to the manifold, pressure transducer means disposed at the opposite end of the second lumen adjacent to the second end of said manifold for detecting pressure in the manifold, second conduit means for conveying gas from the source to the opposite end of said second lumen to clear out the lumen, and second valve means disposed in the said second conduit means for normally blocking the flow of gas therethrough and for periodically opening to allow gas to flow to the second lumen.

2. Apparatus as in claim 1 wherein said manifold further includes an exhaust lumen adjacent the second end thereof open to the outside through which the person may exhale air.

3. Apparatus as in claim 2 further including third conduit means for conveying gas from the second valve means when it opens to the first valve means to cool the first valve means.

4. Apparatus as in claim 1 further including a housing in which are disposed the first and second valve means and the pressure transducer, said housing including conduit connectors for connecting the first and second valve means to the first and second conduit means respectively, and lumen connectors for connecting the first and second valve means to the first and second lumens respectively.

5. Apparatus as in claim 1 wherein first valve means comprises an anvil disposed in contact with one side of the first conduit means, and solenoid means having a movable armature for periodically contacting the other side of the first conduit means to press and pinch it against the anvil to interrupt the flow of gas in the conduit means.

* * * * *